(12) United States Patent
Bartholeyns et al.

(10) Patent No.: US 6,713,056 B1
(45) Date of Patent: Mar. 30, 2004

(54) COMBINED PREPARATION FOR THE TREATMENT OF NEOPLASIC DISEASES OR OF INFECTIOUS DISEASES

(75) Inventors: Jacques Bartholeyns, Bures-sur-Yvette (FR); Yves Fouron, Marlborough, MA (US); Jean-Loup Romet-Lemonne, Paris (FR)

(73) Assignee: I.D.M. Immuno-Designed Molecules, Paris (FR)

( * ) Notice: Subject to any disclaimer, the term of this patent is extended or adjusted under 35 U.S.C. 154(b) by 0 days.

(21) Appl. No.: 09/647,529

(22) PCT Filed: Mar. 29, 1999

(86) PCT No.: PCT/EP99/02105

§ 371 (c)(1),
(2), (4) Date: Nov. 29, 2000

(87) PCT Pub. No.: WO99/51248

PCT Pub. Date: Oct. 14, 1999

(30) Foreign Application Priority Data

Apr. 2, 1998 (EP) .............................. 98400783

(51) Int. Cl.$^7$ .......................... A61K 35/14; C12N 5/08
(52) U.S. Cl. ..................... 424/93.71; 435/2; 435/372; 424/534; 424/93.7
(58) Field of Search .................... 424/158.1, 93.7, 424/93.71, 534; 435/335, 158.1, 2, 372

(56) References Cited

FOREIGN PATENT DOCUMENTS

WO   WO 96/22781   8/1996

OTHER PUBLICATIONS

Fidler and Kleinerman, J. Clin. Oncol., 1984, 2:937–943.*
Silagi, et al., Int J Cancer, 1988, 41:315–322.*
Schachter, et al., 1998, Cancer biotherapy and Radiopharmaceuticals 13: 155–164.*
Williams, et al., 1997, Br J Haematol, 98(4):960–8.*
By B. Hennemann et al., "Monocyte/Macrophage Activation by Immunostimulators: Role in Cancer Therapy", *Clinical Immunotherapeutics*, 1996, pp. 294–308.
By B. Hennemann et al., "Adoptive Immunotherapy with Tumor–Cytotoxic Macrophages Dervied from Recombinant Human Granulocyte–Macrophage Colony–Stimulating Factor (rhuGM–CSF) Mobilized Peripheral Blood Monocytes", *Journal of Immunotherapy*, 1997, pp. 365–361.
By J. Bartoleyns et al., "Immune Therapy with Macrophages: Present Status and Critical Requirements for Implementation", *Immunology*, 1996, pp. 550550–562.
By T. Takeda et al., "The effect of local immunotherapy for breast cancer using a mixture of OK–432 and fibrinogen supplemented with activated macrophages", *Biotherapy*, 1994, pp. 47–54.

* cited by examiner

Primary Examiner—Mary E. Mosher
Assistant Examiner—Misook Yu
(74) Attorney, Agent, or Firm—Young & Thompson

(57) ABSTRACT

The present invention relates to combined preparation containing as active substance the following individual components, in the form of a kit-of-parts: monocyte derived cells, particularly cytotoxic macrophages, chemotherapy or immunotherapy drugs, for the simultaneous, separate or sequential use, for the treatment of cancer or infectious diseases.

25 Claims, 2 Drawing Sheets

COMBINED PREPARATION FOR THE TREATMENT OF NEOPLASIC DISEASES OR OF INFECTIOUS DISEASES

This is a 371 of PCT/EP99/02105, filed Mar. 29, 1999.

The present invention relates to a new combined preparation for the treatment of neoplasic diseases or of infectious diseases.

The present invention describes sequences of conventional treatments of cancer or infections and of immunotherapies reversing or preventing chemoresistance and allowing long lasting therapeutic responses.

BACKGROUND OF THE INVENTION

In conventional therapy, residual tumor cells or infectious agents are left undamaged due to chemoresistance or due to the fact that these cells are shaded in protected areas or located in hypoxic areas poorly vascularized and not accessible to conventional treatments. The genetic instability and heterogeneity of tumors and micro-organisms indeed allow them to adapt and to develop resistance to therapies.

The beneficial effects of chemotherapy can be compromised by cellular mechanisms that allow infectious agents or neoplasic tissue to evade the toxicity of drugs. In some cases, pleiotropic resistance to a variety of unrelated drugs has been observed, and this phenomenon has been called multidrug resistance.

Resistance to chemotherapy, whether it is intrinsic or acquired, is a major cause of failure in the curative treatment of chronic infections or neoplasic malignancies. Among the most active anti-cancer agents used in the treatment of haematological malignancies are some natural toxin-derived drugs, such as the anthracycline daunorubicin or adriamicin, the epipodophyllotoxins, taxoter derivatives, the vinca alkaloid vincristine, cisplatin, fluorouracils.

Development of cross-resistance to these structurally and functionally unrelated drugs, called multidrug resistance, is frequently observed in second or third intention cytotoxic treatment of cancer.

Multiple drug resistance of infectious agents and particularly of bacteria to antibiotics such as penicillins, β-lactamines, cephalosporines, aminoglucosides, macrolides and sulfamides, is more and more often seen in hospitals.

Monocyte derived cells (MDCs) are immune cells such as obtained by culture of blood mononuclear cells in non adherent gas permeable plastic or Teflon bags for 5 to 10 days at 37° C. in $O_2/CO_2$ atmosphere. Their culture medium (RPMI, IMDM, AIM5 (Gibco) or X-VIVO (Biowhittaker)) contains eventually cytokines or ligands as defined in patents PCT/EP93/01232, WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159: 29–38, 1993);

"Immune therapy with macrophages: Present status and critical requirements for implementation" (Bartholeyns J., Romet-Lemonne J-L., Chokri M., Lopez M.; Immunobiol., 195: 550–562, 1996);

"In vitro generation of CD83+ human blood dendritic cells for active tumor immunotherapy" (Thurnher M., Papesh C., Ramoner R., Gastlt G. and al.; Experimental Hematology, 25: 232–237, 1997);

"Dendritic cells as adjuvants for immune-mediated resistance to tumors" (Schuler G. and Steinman R. M.; J. Exp. Med., 186: 1183–1187, 1997).

All these patents applications and articles are included herein for references.

They can be activated by IFN-γ at the end of culture to obtain in particular cytotoxic macrophages. They can be centrifuged to be concentrated and purified before resuspension in isotonic solution.

Monocyte derived cells (MDCs) can either be killer macrophages, phagocytozing cells, growth factors and cytokines releasing cells, or dendritic cells according to their conditions of differentiation. Dendritic cells can for example be obtained as described in "In vitro generation of CD83+ human blood dendritic cells for active tumor immunotherapy" (Thurnher M., Papesh C., Ramoner R., Gastlt G. and al.; Experimental Hematology, 25: 232–237, 1997) and "Dendritic cells as adjuvants for immune-mediated resistance to tumors" (Schuler G. and Steinman R. M.; J. Exp. Med., 186: 1183–1187, 1997), and EP 97/02703.

In addition, activated monocyte derived cells (macrophages) can be used to deliver therapeutic agents to tumor or infectious sites.

BRIEF SUMMARY OF THE INVENTION

One of the aims of the invention is to provide a combined preparation of active substances under the form of individual components for the simultaneous separate or sequential use, in the treatment of cancer or of infectious diseases.

Another aim of the invention is to provide a method for the treatment of residual cancer resistant to chemotherapy.

Another aim of the invention is to provide a method for the treatment of infectious diseases resistant to antibiotic treatment.

The invention relates to a combined preparation containing, as active substance, the following individual components, in the form of a kit-of-parts:

monocyte derived cells, particularly cytotoxic macrophages, chemotherapy or immunotherapy drugs, for the simultaneous, separate or sequential use, for the treatment of cancer or infectious diseases.

BRIEF DESCRIPTION OF THE FIGURES

The present treatment consists in the local or systemic injection of autologous activated macrophages (MAK® killer cells) or monocyte derived cells which have access to injured areas, and in particular to hypoxic areas, where they tend to concentrate.

This treatment can be conducted after first failure and relapse following chemotherapies, or before chemotherapy, to prevent chemoresistance. Local treatment with chemotherapy drugs causes cell necrosis and release of chemokines which call and actively recruit macrophages and monocyte derived cells. Therefore, combining the chemotherapy with macrophage immunotherapy can in synergy increase cytotoxicity and increase immune response at the same time as preventing the establishment of resistance. Additionally to a first treatment combining conventional approach with immunotherapy, macrophage adoptive therapy can be proposed after failure and relapse.

Figure 1:
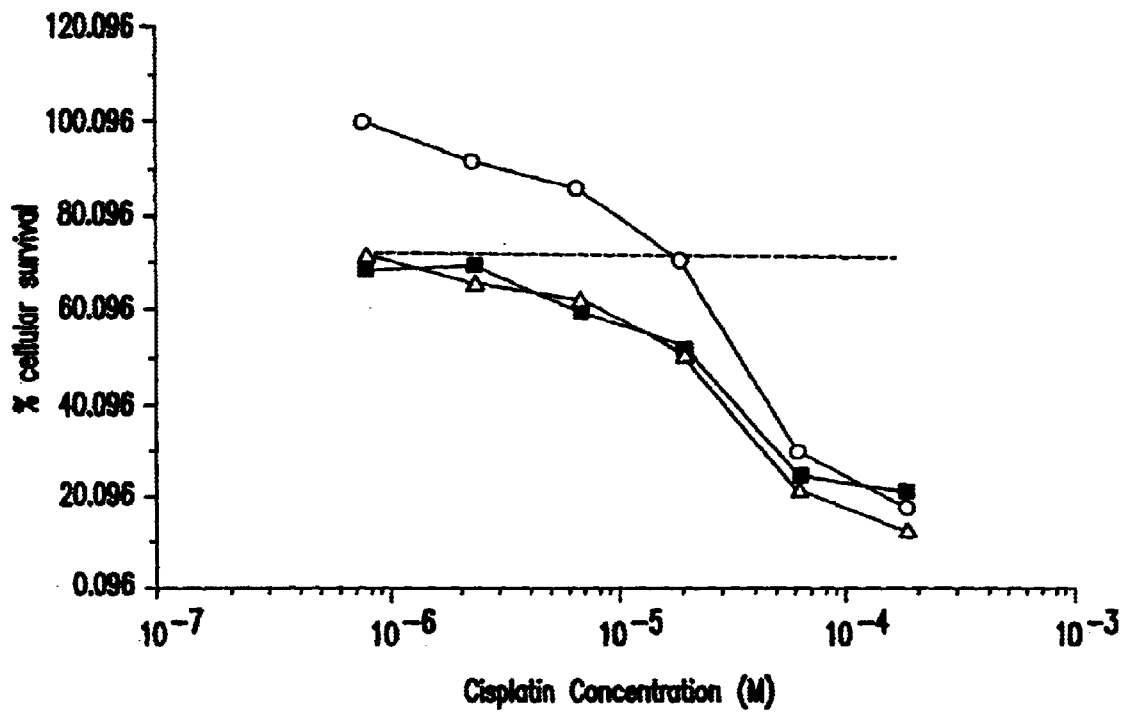

It is shown through the invention that the local or systemic injection of activated monocyte derived cells, or macrophages, restores clinical responses to cytotoxic drugs for which resistance was previously demonstrated, or prevents the apparition of chemoresistance.

The present invention also shows that activated monocyte derived cells can overcome this resistance and synergize for therapy.

The two active ingredients of the combined preparation have never been used for a new joint effect and are unknown as a composition.

The active ingredients which are administered either at the same time, or separately, or sequentially, according to the invention, do not represent a mere aggregate of known agents, but a new combination with the surprising valuable property that immunotherapy with monocyte derived cells modifies the chemoresistance/chemosensitivity and allows a new effective treatment (partial or complete response) with similar chemotherapy protocol. Furthermore, synergy is observed between monocyte derived cells immunotherapy and chemotherapy.

It is to be stressed that the combined preparation also designated by a kit-of-parts means that the components of the combined preparation are not necessarily present as a union e.g. in composition, in order to be available for separate or sequential application. Thus the expression kit-of-parts means that it is not necessarily a true combination, in view of the physical separation of the components.

In an advantageous combined preparation of the invention, the monocyte derived cells contain chemotherapy or immunotherapy drugs.

In another advantageous combined preparation of the invention, the monocyte derived cells are such as prepared according to the method comprising the following steps:
1) recovery of blood derived mononuclear cells directly from blood apheresis or from blood bag collection, followed if necessary by centrifugation, to eliminate a substantial part of red blood cells, granulocytes and platelets, and collection of peripheral blood leukocytes;
2) washing peripheral blood leukocytes obtained at the preceeding steps for instance by centrifugation (to remove 90% of platelets, red blood cells and debris) to obtain mononuclear cells;
3) resuspension of the total mononuclear cells (monocytes+lymphocytes) obtained at the preceeding step in culture medium (RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes.

According to an advantageous combined preparation, the chemotherapy drug is selected among cytotoxic compounds such as anthracyclins, daunorubicin, adriamycin, taxoter derivatives, vinca alcaloids, vincristine, carmustine, cisplatin, fluorouracils, cytostatic compounds such as polyamine inhibitors, topoisomerase inhibitors, tamoxifene, prodasone, or sandostatine, or compounds inducing apoptosis such as sodium butyrate or mitomycin C, antibiotics such as penicilins, β-lactamines, cephasporines, cyclines, arninoglucosides, macrolides or sulfamides, or antiviral drugs such as AZT, protease inhibitors or acyclovir, retrovir or foscarnet.

According to an advantageous embodiment, the combined preparation of the invention is such that the immunotherapy drug is selected among cytokines such as cyclosporine, azathioprine, cyclophosphamide, IFNγ, IL-12, IL-2, GM-CSF, G-CSF, adjuvants such as murapeptides or BCG, or vaccines with or without substances with adjuvant effect. The vaccines can be constituted by tumor or infectious antigens which are of natural, recombinant or gene transfer origin, formulated in the presence or not of an adjuvant for the administration to humans. The vaccine can also be a nucleic acid coding for the antigen or a fragment of antigen, or a virus expressing the antigen.

According to an advantageous embodiment, in the combined preparation of the invention, the monocyte derived cells and the chemotherapy or immnunotherapy drugs are in the form in injectable solutions.

In another advantageous embodiment of the invention, in the combined preparation, the injectable solutions are in the form of locally injectable solutions.

In another advantageous embodiment in the combined preparation of the invention, the injectable solutions are in the form of systemically injectable solutions.

In another advantageous combined preparation of the invention, the monocyte derived cells are administered at a dose of about $10^7$ to about $10^{10}$ monocyte derived cells per injection.

In another advantageous combined preparation of the invention, the monocyte derived cells are administrated at a dose of about $10^8$ to about $10^9$.

In another advantageous combined preparation of the invention, the monocyte derived cells are administered in a repeated way up to ten times, the interval between each administration being between three days to two months.

In another advantageous combined preparation of the invention, the immunotherapy or chemotherapy drug is administered at a dose of about 0.1 to about 1000 mg/day.

In another advantageous combined preparation of the invention, in the case of administration of a drug chosen among immunotherapy drug, antiviral drug, cytotoxic drugs, or antibiotics, said drug is administered at a dose of about 10 to about 1000 mg/day.

More specifically, in the case of cytotoxic compounds such as vincristine, taxol, carmustine, daunorubicin, adryamicin, cisplatin, fluorouracil, they are administered at a dose of about 10 to about 500 mg/day.

In the case of antiviral drugs such as retrovir, aciclovir, foscarnet, said drug is administered at a dose of about 20 to about 500 mg/day.

In the case of antibiotics such as penicilins, cephalosporine, sulfamides, cyclines, said drug is administered at a dose of about 10 to about 1000 mg/day.

In the case of immunotherapy drugs such as cyclosporine, azathioprine, cyclophosphamide, said drug is administered at a dose of about 10 to about 1000 mg/day.

In another advantageous combined preparation of the invention, in the case of administration of a drug chosen among cytostatic compounds, apoptosis inducing compounds or cytokines, said drug is administered at a dose of about 0.1 to about 100 mg/day.

In the case of cytostatic compounds such as amoxifene, prodasone, sandostatine, polyamine inhibitors or apoptosis inducing compounds such as sodium butyrate or mitomycin C, said drug is administered at a dose of about 0.1 to about 100 mg/day.

In another advantageous combined preparation of the invention, the immunotherapy or chemotherapy drug is administered in a repeated way up to 10 times, the interval between each administration being between one day to two months.

In another advantageous combined preparation of the invention, the chemotherapy or immunotherapy drug and the monocyte derived cells are injected simultaneously.

In another advantageous combined preparation of the invention, the chemotherapy or immunotherapy drug and the monocyte derived cells are administered in sequential way, the immunotherapy or chemotherapy drug being administered before the monocyte derived cells.

In another advantageous combined preparation of the invention, the interval of time between the administration of the monocyte derived cells and the administration of the immunotherapy or chemotherapy drugs is of one day to two months.

In another advantageous combined preparation of the invention, the monocyte derived cells and the chemotherapy or immunotherapy drug are administered seqentially, the monocytes derived cells being administered before the immunotherapy or chemotherapy drug.

In another advantageous combined preparation of the invention, the monocyte derived cells are administered before the administration of a vaccine directed to tumor or infectious antigens, the monocyte derived cells administration being possibly preceded by a chemotherapy treatment.

In an advantageous embodiment of the invention, the monocyte derived cells are administered before the administration of the vaccine, the time internal between the respective administrations being for example of one week to three months. The vaccine administration can be repeated several times for optimal immunisation, according to classical procedures. In this case, the monocyte derived cells administration can be considered as a priming for the reaction to the antigen and the administration(s) of the vaccine as a boost of the immune responses.

In another advantageous embodiment of the invention, the patients are first treated by conventional chemotherapy drugs, this treatment being followed sequentially by administration of monocyte derived cells and then by the vaccine administration as a boost, to induce optimal immunization against cancer or infectious disease.

In another advantageous combined preparation of the invention, the interval of time between the administration of the immunotherapy or chemotherapy drug and the administration of the monocyte derived cells is of one day to two months.

In another advantageous combined preparation of the invention, the administration of monocyte derived cells is followed by an administration of chemotherapy or immunotherapy drug.

In another advantageous combined preparation of the invention, the interval of time between the administration of monocyte derived cells and the administration of chemotherapy or immunotherapy drugs is of one day to two months.

The invention also relates to a method for the treatment of residual cancer resistant to chemotherapy or of infectious diseases resistant to chemotherapy comprising the use of a combined preparation of the invention.

The invention also relates to a method for the treatment of infectious diseases resistant to antibiotic treatment comprising the use of a combined preparation of the invention.

The monocytes derived cells which are involved in the invention, can be activated macrophages and/or monocytes derived antigen presenting cells.

According to an advantageous embodiment, the combined preparation of the invention comprises monocyte derived cells, loaded with a complex mixture of antigens, and a vaccine containing purified antigens.

The monocyte derived cells loaded with a complex mixture of antigens will be also referred to as "the cellular vaccine".

The monocyte derived cells can be macrophages or dendritic cells derived from blood monocytes, preferably cultured in the presence of lymphocytes.

The expression "a complex mixture of antigens" designates antigens with a large spectrum of specificity for the infectious agent or the tumor cells.

As to the vaccine containing purified antigens, its specificity is restricted to one or a few epitopes of the target agent (infectious agent or tumor cells).

According to an advantageous embodiment, when the macrophages or dendritic cells derived from blood monocytes are cultured in the presence of lymphocytes, said lymphocytes are T lymphocytes ($CD4^+$ and $CD8^+$ types) and natural killer cells (NK cells) generated during the coculture. These lymphocytes and NK cells can be recovered and possibly expanded ex vivo, for simultaneous or sequential injection with said monocyte derived cells (loaded with a complex mixture of antigens).

In a particular embodiment, immunomonitoring of patients treated with vaccines containing purified antigens, allows detection and identification of the specific cellular response to conventional antigens. The useful specific T cell response can be amplified ex vivo. Monocyte derived cells presenting a mixture of complementary antigens can then be designed to avoid the development of immunoresistant viruses or tumors.

In the optimal sequence of said cellular vaccine and said vaccine containing purified antigens, said vaccine containing purified antigens is used as a boost to achieve immune memory against the targeted infectious or tumor disease.

The above defined combined preparation of the invention induces cellular and humoral responses to cancer and viral antigens.

According to another advantageous embodiment, the vaccine containing purified antigens is injected first, followed by the injection of the cellular vaccine.

Figure 2:
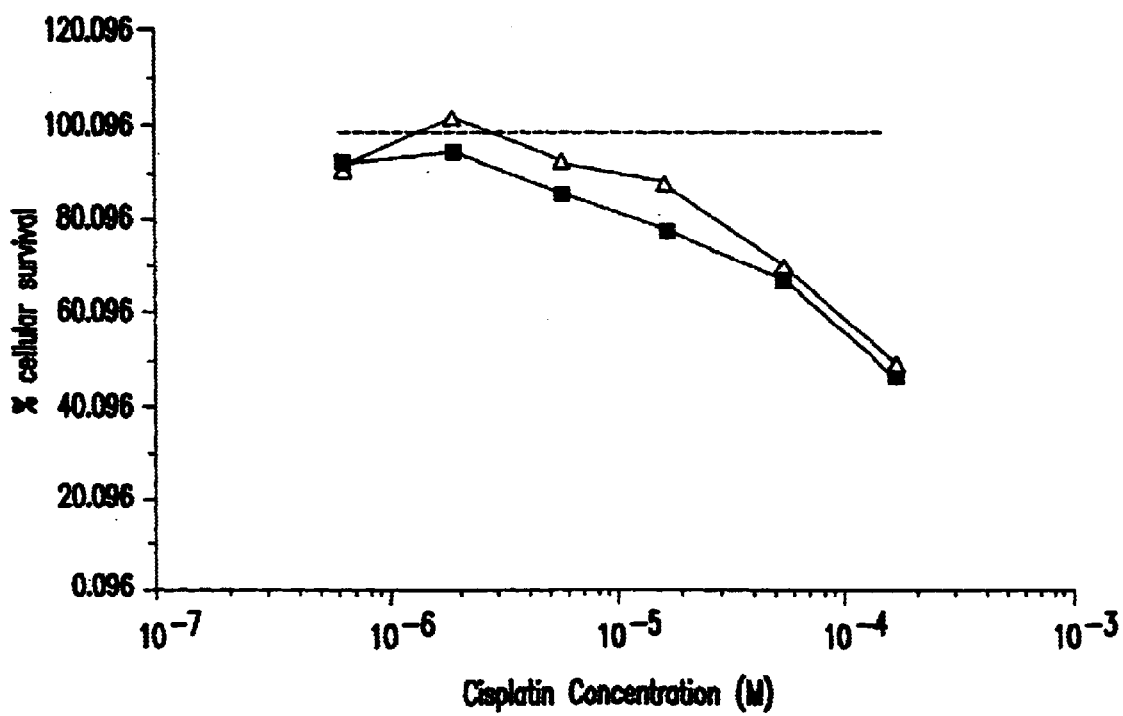

FIGS. 1 and 2 represent the in vitro synergy between chemotherapy (use of cisplatin) and macrophages (MAK) cytotoxicity on human ovary carcinoma tumor (IGR-OV1).

FIG. 1 corresponds to chemosensitive tumor and FIG. 2 corresponds to chemoresistant tumor.

Tumor cells have been grown for 3 days of cocultured at 37° C., 5% $CO_2$ from an initial seeding of $10^5$ cells under the following conditions:
  presence of cisplatin,
  presence of human macrophages,
  presence of cisplatin and human macrophages.

The percentage of tumor cell survival is measured according to the method described in "Feasibility of drug screening with panels of human tumor cell lines using a microculture tetrazolium assay" (Alley M. C., Scudiero D. A., Monks A., et al.; Cancer Res., 1988, 48: 489–501), and is plotted against the dose of cisplatin (abscissa) in the test tube (molar concentration).

The amount of macrophages used in the experiment is constant.

The initial ratio between macrophage and tumor cells is 4/1 for FIG. 1, and 1/1 in FIG. 2.

The dotted line corresponds to the addition of macrophages alone.

The open circle curve corresponds to the addition of cisplatin alone.

The dark square curve corresponds to the addition of macrophages and cisplatin.

The open triangle curve corresponds to the theoretical addition of the effects of macrophages alone, plus cisplatin alone.

On FIG. 2, the open circle curve and the open triangle curve are superimposed.

Additive effects of macrophages and cisplatin are seen on chemosensitive tumor cells. Synergy or potentiation of macrophages and cisplatin is observed for the chemoresistant tumor.

Figure 3:
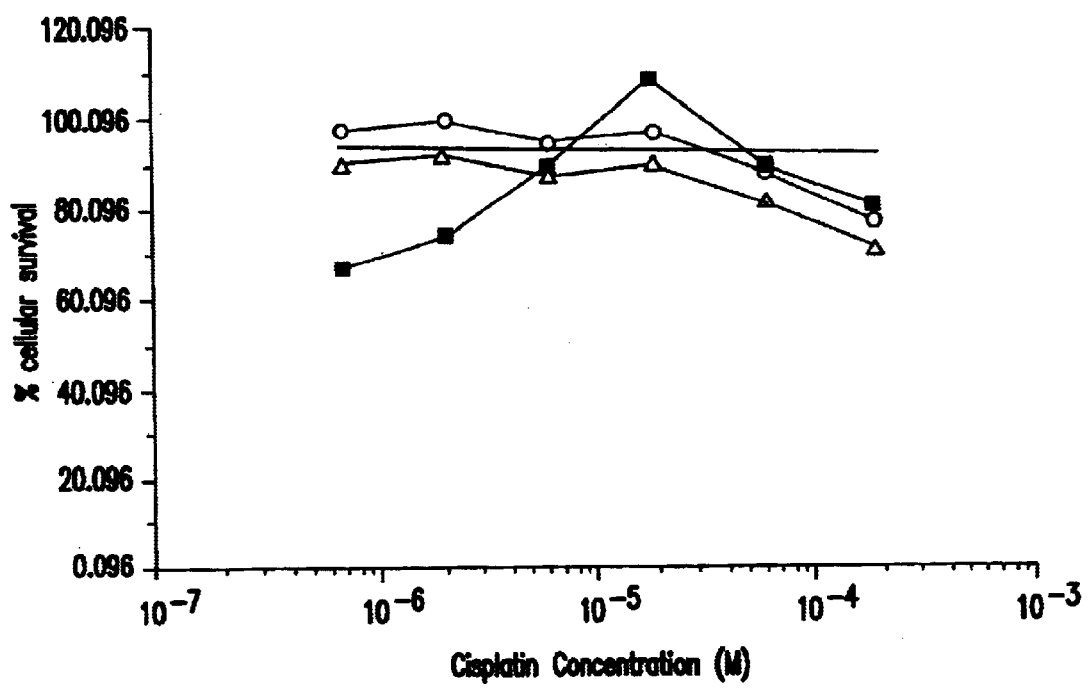

FIG. 3 represents the percentage of cellular survival as a function of cisplatin concentration (M).

The curve with hollow circles corresponds to the use of cisplatin alone.

The plain curve corresponds to the use of MAK alone.

The curve with black squares corresponds to the use of the combination of MAK followed by cisplatin.

The curve with hollow triangles corresponds to the theoretical additive curve of a treatment with MAK alone and a treatment with cisplatin alone.

EXAMPLES

The following examples describe some applications of the invention:

1) The synergy between macrophage immunotherapy and chemotherapy has been demonstrated in vitro on a carcinoma tumor cell line. Relative sensitivity of a human ovary tumor cell line and a derived line resistant to cisplatinum is documented, as well as the cytotoxicity of activated macrophages on these lines. Additive antitumoral effects for macrophages and cisplatinum is documented, allowing an effective dose response with lower levels of the drug, as demonstrated in FIG. 1 and FIG. 2.

16R-OV1/DDP human ovary cancer cell line was rendered resistant to cisplatinum by continuous exposure to increasing concentrations of cisplatin (Fajac A., et al. Cisplatin induced apoptosis and p.53 gene status in a cisplatin resistant human ovarian carcinoma cell line. Int. J. Cancer 68, 67–74, 1996). The cells are grown at 37° C., 5% $CO_2$ in RPMI 1640 medium in the presence of activated human macrophages (MAK) during 24 hours and then with cisplatin at increasing concentrations. Cisplatin alone (O) inhibited survival by 35% at maximal dose ($10^{-3}$M, see FIG. 3). Activated macrophages inhibited survival by 10% (effector/tumor ratio 4, basal line). The combination of MAK and of a low dose cisplatin ($10^{-6}$M) inhibited survival by 40% (■). The sequential combination of MAK and cisplatin (MAK followed by cisplatin) acted in synergy since the cytotoxicity was much higher at low cisplatin dose than the theoretical additive curve of both treatments (Δ, see FIG. 3).

2) Nude mice inoculated with human carcinoma solid tumors are initially treated with cytotoxic drugs (Adriamycin, Etretinate, Taxotere), used alone or in combination. After a first response, the tumors grow again and the animals are treated systemically, or locally by injection of 1 million activated human macrophages which allow tumor stabilization. A second treatment with the same cytotoxic drugs used initially allow further antitumoral effect documented by measurement of subcutaneous tumor size.

3) Three patients with colorectal cancer and four patients with lung mesothelioma became resistant to 5-fluorouracil+Cisplatin (or its oxaliplatin derivative) chemotherapy. They then have been injected with autologous activated macrophages and they have presented tumor stabilization or partial response illustrated by radiography. After a few months, the tumor relapsed and cancer evolution was reported. A second chemotherapy treatment, with similar cocktail of cytotoxic drugs, induced complete responses or major partial responses. This indicates a modification of the chemoresistance caused by immunotherapy.

4) Patients with prostate cancer treated by radio and chemotherapy present a 50% relapse rate of their cancer within 2 years. A treatment with activated macrophages is proposed after the conventional therapy. The time of relapse within 2 years as well as the evolution of the tumor are documented.

5) Bacterial infections induced in nude mice are relatively resistant to antibiotics. Effective therapy is achieved by sequential injection of macrophages and of antibiotics at usually ineffective doses. The additive effects of classical anti-infections drugs and of macrophage immunotherapy are documented.

6) Patients with myeloid leukemia, or with multiple myeloma, are treated with high dose chemotherapy. During the 6 weeks of aplasia, they present multiple infections, in particular nosocomial infections. Injections of activated macrophages during this period is performed to prevent infections and to allow a cure at lower doses of antibiotics.

7) C57B16 mice bearing solid carcinoma are injected intraperitonealy with a drug inducing apoptosis (1 mg mitomycin C or 0.1 mg sodium butyrate). After 24 h, mice are injected with 0.1 million monocyte derived cells in tumor periphery. Tumor regression and protection against further tumor challenge is observed only after this combined treatment. In another protocol, carcinoma cells are treated in vitro with 0.01 mM sodium butyrate, and then submitted to phagocytosis by murine monocyte derived cells. Injection of mice with 0.1 million of these monocyte derived cells protects the animals against carcinoma challenge.

8) Dendritic cells (DC) are obtained from bone marrow precursors of Balb/c syngeneic mice after 7 days of culture in medium supplemented with GM-CSF and IL-13. The dendritic cells are loaded with the S protein of the hepatitis B virus at 20 μg/ml for 4 hours. One million cells are injected intravenously. 7 days later, a mixture of HBS protein and adjuvant is injected in the peritoneal cavity. At day 15, the immune response is assessed by two different methods:

serum titer of antibody against HBS is measured by ELISA, the spleen from the mice is removed and T lymphocytes are stimulated with irradiated isogenic splenocytes loaded with peptides for 7 days. At day 22, the significant cytotoxic activity of the T lymphocytes is measured using as targets p815 cells loaded with the 28-39 peptide (an immunogenic peptide of the S antigen).

9) Patients, whose primary melanoma tumor was removed by surgery, are treated with chemotherapy agent (DTIC) (dacarbazine) after relapse. When their blood count is back to normal, blood is drawn up through apheresis in order to prepare large amounts of MD-APCs. These cells are then incubated for 4 hours with allogeneic tumor extract. 3 weekly sub-cutaneous injections (at 4 different sites) of $10^7$ cells are made. Two months later, a cocktail of three antigens (MAGE-3, MELAN A and gp-100) (Boon et al. Immunology today, June 1997, Vol. 18, n 6, 267) plus adjuvant is injected to the patients in order to boost the immune system. The increased immune response is monitored by measuring the number of antigen specific CD8 T lymphocytes by ELISPOT technique (Herr. et al. Detection and quantification of blood-derived CD8+ T lymphocytes secreting tumor necrosis factor alpha in response to HLA-A2.1-binding melanoma and viral peptide antigens. J Immunol Methods 191, no. 2:131–42.) It is also assessed that the relapse-free time is significantly increased.

In a particular embodiment of the invention, macrophages are loaded ex vivo with a drug as promyxin (a bioreductive agent) active in hypoxic areas. In this case, the macrophages having been fed with the drug, concentrate in the necrotic/hypoxic area, kill tumor cells in contact and release locally during several days the cytotoxic drug killing the remaining cancer cells. A radiotherapy enhancer (tirazone) is also loaded into macrophages which cause, after reinjection, a potentiation of radiotherapy at specific tumor sites.

In another embodiment of the invention, an antibiotic is loaded into macrophages from patients with nosocomial infections resistant to conventional antibiotics.

The proper sequence and timing of macrophages injections, allowing maximum activity at the tumor or infectious site, are disclosed.

What is claimed is:

1. Preparation comprising the following individual components, in the form of a kit:
    monocyte derived cells which have been in culture for 5 to 10 days, and
    chemotherapy drugs,
    for the simultaneous, separate or sequential use, for the treatment of cancer or infectious diseases in a patient.

2. Preparation according to claim 1, wherein the monocyte derived cells are prepared according to the method comprising the following steps:
    1) recovering blood derived mononuclear cells directly from blood apheresis or from blood bag collection, followed if necessary by centrifugation, to eliminate the red blood cells granulocytes and platelets, and collection of peripheral blood leukocytes;
    2) washing peripheral blood leukocytes obtained at the preceding steps by centrifugation (to remove 90% of platelets, red blood cells and debris) to obtain mononuclear cells;
    3) resuspending the total mononuclear cells (monocytes+lymphocytes) obtained at the preceding step in culture medium (RPMI or IMDM type) at $10^6$ to $2.10^7$ cells/ml, completed by at least one of cytokines and autologous serum, and culture at 37° C. under $O_2/CO_2$ atmosphere in hydrophobic gas permeable bags, to obtain monocyte derived cells and contaminating lymphocytes.

3. Preparation according to claim 1, wherein the chemotherapy drug is selected from the group of compounds consisting of anthracyclins, daunorubicin, adriamycin, taxoter derivatives, vinca alcaloids, vincristine, taxol, carmustine, cisplatin, fluorouracils, polyamine inhibitors, topoisomerase inhibitors, tamoxifene, prodasone, sandostatine, sodium butyrate, mitomycin C, penicillins, β-lactamines, cephalosporines, cyclines, aminoglucosides, macrolides, sulfamides, AZT, protease inhibitors, acyclovir, retrovir and foscarnet.

4. Preparation according to claim 1, wherein the monocyte derived cells and the chemotherapy drugs are in the form of injectable solutions.

5. Preparation according to claim 4, wherein the form of injectable solutions are for locally injectable solutions.

6. Preparation according to claim 4, wherein the form of injectable solutions permit systemically injectable solutions.

7. A process for preparing monocyte derived cells and chemotherapy drugs in the form of a kit for simultaneous, separate, or sequential use for the treatment of cancer or infectious diseases in a patient, comprising the following steps:
    1) recovering blood derived mononuclear cells directly from blood apheresis or from blood bag collection, followed if necessary by centrifugation, to eliminate the red blood cells granulocytes and platelets, and collection of peripheral blood leukocytes;
    2) washing peripheral blood leukocytes obtained at the preceding steps by centrifugation (to remove 90% of platelets, red blood cells and debris) to obtain mononuclear cells;
    3) resuspending the total mononuclear cells (monocytes+lymphocytes) obtained at the preceding step in culture medium (RPMI or IMDM type) at $10^6$ to $2.10^7$ cells/ml, completed by at least one of cytokines and autologous serum, and culture at 37° C. under $O_2/CO_2$ atmosphere in hydrophobic gas permeable bags, to obtain monocyte derived cells and contaminating lymphocytes; and
    4) assembling said monocvte derived cells in a kit with chemotherapy drugs.

8. The process according to claim 7, further comprising centrifuging said monocyte derived cells, washing, and resuspending said monocyte derived cells to obtain a suspension of the monocyte derived cells.

9. The process according to claim 8, further comprising the additional step of freezing said suspension at a temperature below or equal to −80° C. aliquots with the addition of a cryopreservative.

10. The process according to claim 9, further comprising melting said frozen aliquots to obtain a suspension of monocyte derived cells, washing said suspension, and resuspending said suspension in an isotonic medium to obtain a suspension of monocyte derived cells.

11. Process for the simultaneous, separate, or sequential use of a preparation for the treatment of cancer or infectious diseases in a patient, comprising:
    administering to said patient an effective amount of said preparation, wherein said preparation comprises the following individual components, in the form of a kit:
    monocyte derived cells which have been in culture for 5–10 days, and
    chemotherapy drugs.

12. The process according to claim 11, wherein the monocyte derived cells are administered at a dose from $10^7$ to $10^{10}$ monocyte derived cells per injection.

13. The process according to claim 12, wherein the monocyte derived cells are administered at a dose from $10^8$ to $10^9$.

14. The process according to claim 12, wherein the monocyte derived cells are administered repeatedly up to ten times, the interval between each administration being between three days to two months.

15. The process according to claim 11, wherein the chemotherapy drug is administered at a dose of 0.1 to 1000 mg/day.

16. The process according to claim 11, wherein in the case of administration of a drug, said drug is selected from the group consisting of cytotoxic compounds, cytostatic compounds, compounds inducing apoptosis or cytokines, said drug administered at a dose of 0.1 to 100 mg/day.

17. The process according to claim 11, wherein the chemotherapy drug is administered repeatedly up to 10 times, the interval between each administration being between one day to two months.

18. The process according to claim 11, wherein the chemotherapy drug and the monocyte derived cells are injected simultaneously.

19. The process according to claim 11, wherein the chemotherapy drug and the monocyte derived cells are administered sequentially, the chemotherapy drug being administered before the monocyte derived cells.

20. The process according to claim 19, wherein the interval of time between the administration of the monocyte derived cells and the administration of the chemotherapy drugs is of one day to two months.

21. The process according to claim 11, wherein the monocyte derived cells and the chemotherapy drug are administered sequentially, the monocyte derived cells being administered before the chemotherapy drug.

22. The process according to claim 11, wherein the monocyte derived cells are administered before the administration of a vaccine directed to tumor or infectious antigens, the monocyte derived cells administration being preceded by a chemotherapy treatment.

23. The process according to claim 22, wherein the interval of time between the administration of the chemotherapy drug and the administration of the monocyte derived cells is one day to two months.

24. The process according to claim 19, wherein the administration of monocyte derived cells is followed by an administration of the chemotherapy drug.

25. The process according to claim 24, wherein the interval of time between the administration of monocyte derived cells and the administration of chemotherapy drugs is one day to two months.

\* \* \* \* \*